Figure 2:
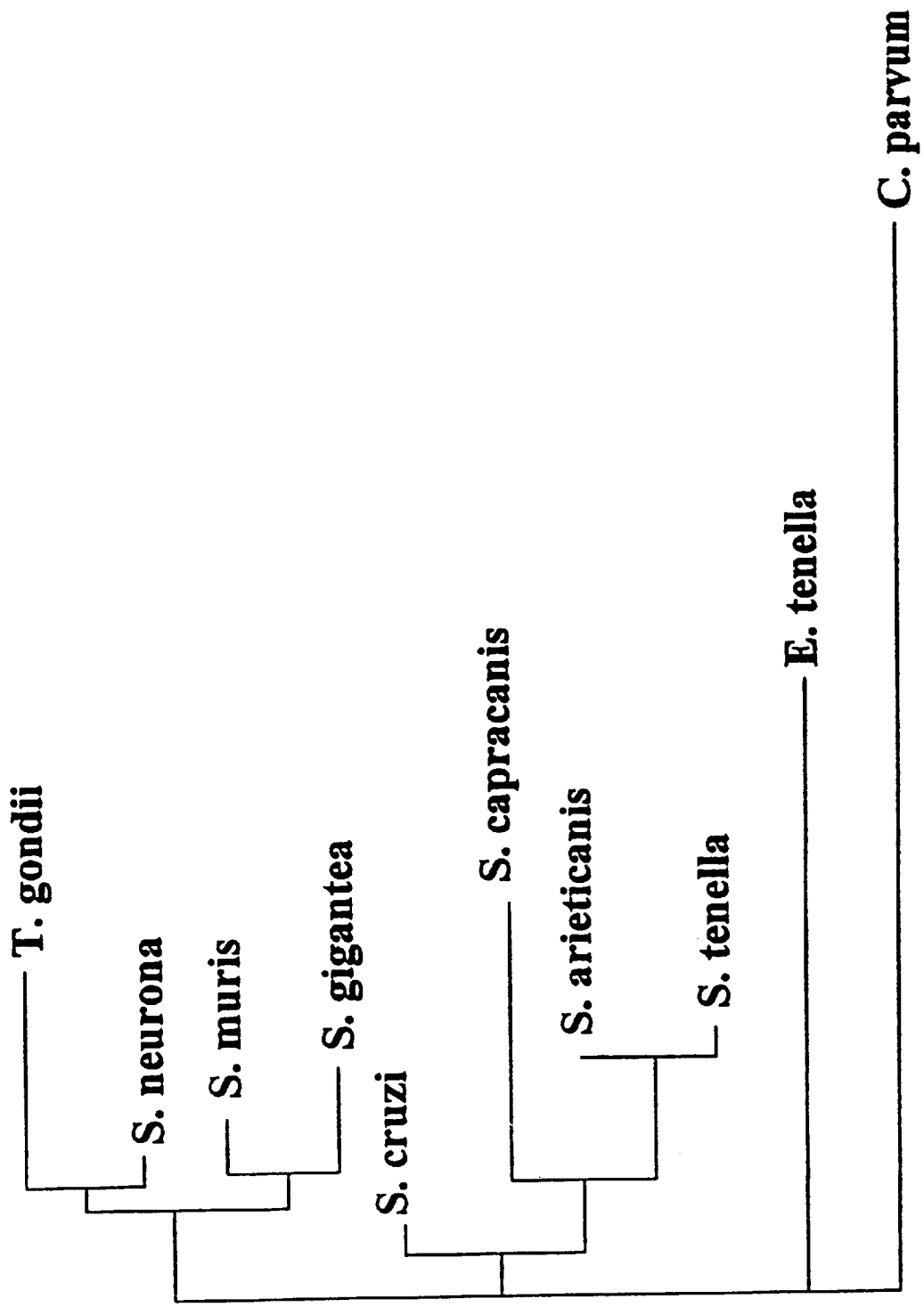

United States Patent [19]
Fenger et al.

[11] Patent Number: 6,110,665
[45] Date of Patent: *Aug. 29, 2000

[54] *SARCOCYSTIS NEURONA* DIAGNOSTIC PRIMER AND ITS USE IN METHODS OF EQUINE PROTOZOAL MYELOENCEPHALITIS DIAGNOSIS

[75] Inventors: Clara K. Fenger; David E. Granstrom; Alvin A. Gajadhar, all of Lexington, Ky.; Jitender P. Dubey, Greenbelt, Md.

[73] Assignee: University of Kentucky Research Foundation, Lexington, Ky.

[ * ] Notice: This patent is subject to a terminal disclaimer.

[21] Appl. No.: 08/388,029

[22] Filed: Feb. 14, 1995

[51] Int. Cl.⁷ .............................. C12Q 1/68; C12P 19/34; C07H 21/04
[52] U.S. Cl. .................... 435/6; 435/91.2; 536/24.32; 536/24.33; 935/8; 935/77; 935/78
[58] Field of Search .................. 435/5, 6, 91.2, 435/235.1, 8, 77, 78; 536/24.32

[56] References Cited

U.S. PATENT DOCUMENTS

| | | | |
|---|---|---|---|
| 4,740,456 | 4/1988 | Kuhn et al. | 435/7 |
| 4,759,927 | 7/1988 | Dutta | 424/88 |
| 5,141,925 | 8/1992 | Alroy et al. | 514/23 |
| 5,210,018 | 5/1993 | Nuzzolo et al. | 435/7.22 |
| 5,340,728 | 8/1994 | Grosz et al. | 435/91.2 |

FOREIGN PATENT DOCUMENTS

WO 88/03957  6/1988  WIPO.

OTHER PUBLICATIONS

Abstract of Simpson et al., "Evidence for Sarcocystis as the etiologic agent of equine protozoal myeloencephalitis." J. Protozool., Aug. 1980, 27 (3), pp. 288–292.

Abstract of Hamir et al., "Immunohistochemical study to deomonstrate Sarcocysitis neurona in equine protozoal myeloencephalitis." J. Vet. Diagn. Invest., Jul. 1993, 5 (3), pp. 418–422.

Abstract of Granstrom et al., "Equine protozoal myeloencephalitis: antigen analysis of cultured Sarcocystis neurona merozoites." J. Vet. Diagn. Invest., Jan. 1993, 5 (1), pp. 88–90.

Abstract of Hamir et al., "A five year (1985–1989) retrospective study of equine neurological diseases with special reference to rabies." J. Comp Pathol., May 1992, 106 (4), pp. 411–421.

Abstract of Bowman et al., "Characterization of Sarcocystis neurona from a thoroughbred with equine protozoal myeloencephalitis." Cornell Vet., Jan. 1992, 82 (1) pp. 41–52.

(List continued on next page.)

*Primary Examiner*—W. Gary Jones
*Assistant Examiner*—Debra Shoemaker
*Attorney, Agent, or Firm*—Lowe, Price, LeBlanc & Becker

[57] ABSTRACT

An amplification primer and probe which can be used in an in vitro diagnostic test for the presence of *S. neurona* in equine blood or cerebrospinal fluid. *Sarcocystis neurona* is responsible for the equine condition of protozoal myelitis. The amplification primer is seventeen nucleotides in length and complementary to a unique section of the small ribosomal subunit of *Sarcocystis neurona*. The primer encompasses nucleotide positions 1470–1487 of the small ribosomal subunit of *S. neurona*. The primer has the sequence 5' CCATTCCGGACGCGGGT SEQ ID NO:1.

10 Claims, 7 Drawing Sheets

OTHER PUBLICATIONS

Abstract of Madigan et la., "Equine Protozoal Myeloencephalitis." Vet. Clin. North Am. Equine Pract., Aug. 1987, 3 (2), pp. 397–403.

Abstract of Dubey et al., "Sarcocystis neurona n. sp. (Protozoa: Apicomplexa), the etiologic agent of equine protozoal myeloencephalitis." J. Parasitol, Apr. 1991, 77 (2), pp. 212–8.

Gajadhar et. al. Canadian Journal of Veterinary Research 52:208–213 Jul. 1992.

Granstrom et. al. Molecular and Cellular Probes 8:353–356 Oct. 1994.

Holmdahl et. al. Molecular and Cellulas Probes 7:481–486 Dec. 1993.

Fenger et al. Journal of Parasitology 80(6):966–975 Dec. 1994.

Dame et. al. Journal of Parasitology 81(6):930–935 Dec. 1995.

Tenter et. al. International Journal for Parasitology 22(4):503–513 1992.

Figure 1A

```
POS=604
S. neurona       ATAGTA-ACCGAACGGATCGCA-T-TAT        SEQ ID NO:8
S. muris         ATAGTA-ACCGAACGGATCGCA-C-TAT        SEQ ID NO:9
S. capricanis    ATNTCG-CNNTCTGAGATCGCGAT-NAT        SEQ ID NO:10
S. arieticanis   NTANNANTCCGNNNGGTTCNNN-TNANT        SEQ ID NO:11
S. cruzi         ATAGTA-ACCGAACGGATCGC-AT-TAT        SEQ ID NO:12
S. gigantea      ATAGTA-NCNGAACGGATCGCATCATAT        SEQ ID NO:13
S. tenella       ATNGTNNTCCGTTCN-TTCGTCAT-TNT        SEQ ID NO:14
T. gondii        ATAGTA-ACCGAACGGGTCGCGTTGACT        SEQ ID NO:15
E. tenella       ATAGTA-ACCGAACGGATCGC-AN-GTT        SEQ ID NO:16
C. parvum        ATAATA-ACTTTNCGGATCACATTAAAT        SEQ ID NO:17

POS=661
SN:    GCGATGGATCATTCA-AGTTTCT-GAC-CTATC-AGCT-TTC-GA-CGGTACTGTA     SEQ ID NO:18
SM:    GCGATAGATCATTCA-AGTTTCT-GAC-CTATC-AGCT-TTC-GA-CGGTACTGTA     SEQ ID NO:19
SCA:   GCGATNNNNNTNCN-NGTTTCT-GNC-CTATCNNGCT-TTCNGN-CGGTAGTGTA      SEQ ID NO:20
SA:    GCGTTNGATCATTCN-NGTTTCT-GAC-CTATCNAGCT-TTN-GANCGGTNGTGTN     SEQ ID NO:21
SCR:   GCGATAGATCNTTCA-AGTTTCT-GAC-CTATC-AGCT-TTC-GA-CGGTNGTGTA     SEQ ID NO:22
SG:    GCGATAGATCATTCA-AGTTTCT-GAC-CTATC-AGCT-TTC-NA-CGGTACTGTA     SEQ ID NO:23
ST:    GCGNNGGATNNNNTCGANTNTCTNGACTCTATC-NGCT-T-C-G--CGGTAGTGTA     SEQ ID NO:24
TG:    GCGACGGATCATTCA-AGTTTCT-GAC-CTATC-AGCTATTC-GA-CGGNACTGTA     SEQ ID NO:25
ET:    GCGATGGATCATTNA-AGNTTCT-GAC-CTATCNAGCT-TTC-GA-CGGTAGGNTA     SEQ ID NO:26
CR:    GTGACATATCATTCA-AGTTTCT-GAC-CTATC-AGCT-TTA-GN-CGGTAGGNTA     SEQ ID NO:27
```

Figure 1B

```
POS=735
SN:    TT-GGACTACCGTGTGGCAGTGACGGGTAACGGGGAATTAGGGTTCGATTCC-GG    SEQ ID NO:28
SM:    TT-GGACTACCGTGTGGCAGTGACGGGTAACGGGGAATTAGGGTTCGATTCC-GG    SEQ ID NO:29
SCA:   TT-GG-CTCCCGTGTGGCAGTGCNGTGNNNGGGNATTAGGGTTCGNTTCC-GG      SEQ ID NO:30
SA:    TTNGGACTACCGTGTGGCAGTGNCGGGNNNCGGGNATTAGGGTTCGATTCC-GG     SEQ ID NO:31
SCR:   TT-GGNCTTNCN-TNGCAGTGNCGGGNNN-CGGGNNTTAGGGNTCGNNTCC-GG     SEQ ID NO:32
SG:    TT-GGACTACCNTGGCAGNACGGGNNACGGGAATTAGGGTTCGATTCC-GG        SEQ ID NO:33
ST:    TT-GG-CTNCNNTNGCAGTG-NGGNTNNNGGGGAATTCGGGTTCGATTCC-GG      SEQ ID NO:34
TG:    TT-GGACTACCNTGGCAGNGACGGNTAACGGGGAATNAGNNNTNNATTCC-GN      SEQ ID NO:35
ET:    NT-GGCTACNNTNGCAGTGACGGGNNACGGGGAATTAGGGTTCGATTCC-GG       SEQ ID NO:36
CR:    TT-GGCCTCACNNGGCAATGACGGGTACNNGGGAATTAGGNNTCGATTCCAGG      SEQ ID NO:37

POS=792
SN:    AGA-GGGAGCCT-GAGAAAACGGCTACCACATCTAAGGAAGGCAGCAGGCGCGCA    SEQ ID NO:38
SM:    AGA-GGGAGCCT-GAGAAAACGGCTACCACATCTAAGGAAGGCAGCAGGCGCGCA    SEQ ID NO:39
SCA:   AGA-GGGAGCCT-GAGANNCGGCTNCCNCNTCTNNGGNNGGCNGCNGGCGCGCA     SEQ ID NO:40
SA:    AGNTGGGAGCCT-GAAANNCGGCTNCCACATCCTNN--NNGGCNGCNGGCGCNCA    SEQ ID NO:41
SCR:   AGN-GGGAGCCT-GAGNNNCGGCTNCCNCNTCTNNNGNNGGCNNNNNNNNNCA      SEQ ID NO:42
SG:    AGA-GGGAGCCT-GAGAANCGGCTACCACATCTAAGGN-GGCAGCAGGCGCNCA     SEQ ID NO:43
ST:    AGA-GGGAGCCT-GAGNNNCGGCTACCACATCTNNNNN-GGCNGCNGGCGCNCA     SEQ ID NO:44
TG:    AGA-NNGAGNCT-GANAAACGGCTACCACATCTAAGGAAGGCAGCAGGCGCGCA     SEQ ID NO:45
ET:    AGA-GGGAGCCT-GAGAAAACGGCTACCNNATCTAAGGNNGGCAGCAGGCGCGCA    SEQ ID NO:46
CR:    ANA-GGGAGCCTCGAGAAAACGGCTACCACATNTAAGGAAGGCAGCAGGCGCNCA    SEQ ID NO:47
```

Figure 1C

POS=905
```
SN:   ACAC-TGGAAAATTATATTTCTAGTGATTG-GAATGATGGGAATCCAAACCCCTTT    SEQ ID NO:48
SM:   ACAC-TGGAAAATTCAATTTCTAGTGATTG-GAATGATGGGAATCCAAACCCCTTT    SEQ ID NO:49
SCA:  ACAC-TGGAAAATTCAATTTCTAGTNATTG-GAATGATGGGNATTNNNCCCCTTT     SEQ ID NO:50
SA:   ACNC-TGGAAAATTTTNTTTCTNGTGATTG-GAATGATGGGAATTNNNCCCCTTT     SEQ ID NO:51
SCR:  ACAC-TGGAAAATTTTNTTTCTAGTNATTG-GNATGANGGGNATTNNNCCCNTTT     SEQ ID NO:52
SG:   ACNCNTGGAAAATTGTNTTTCTAGTGATTG-GAATGATGGGAATCCNNNCCCCTTT    SEQ ID NO:53
ST:   ACAC-TGGAAAATTTTATTTCTAGTNATTG-GAATGATGGGAATTNNNCCCNTTT     SEQ ID NO:54
TG:   ACAC-TGGAAAATTTCATTTCTAGTGATTG-GAATGATAGGAATCCAAACCCCTTT    SEQ ID NO:55
ET:   ATACAGGGNA-TTTTATGCTTTGTTGTAATTGG-AATGATGGGAATGTAAAACCCTTT  SEQ ID NO:56
CR:   ATANCTAGGNCTTTTGTTTTTGTNATTGTNATTGTGAATGATGTTAATGTATNCCCCTTT SEQ ID NO:57
```

POS=2108
```
SN:   ATTTAACTGTGAGAGGTGAAATTCTTAGATTTGTTAAAGACG-AA-CTACTGC    SEQ ID NO:58
SM:   ATTTAACTGTCAGAGGTGAAATTCTTAGATTTGTTAAAGACG-AA-CTACTGC    SEQ ID NO:59
SCA:  ATTTAACTNN-AGAGGTGAAATTCTTAGATTTGTTAAAGACG-AA-CTACTGC    SEQ ID NO:60
SA:   ATTTAACTNTNAGAGGTGAAATTCTTAGATTTGTTAAAGACG-A-CCTNCTGC    SEQ ID NO:61
SCR:  ATTTAACTNN-AGAGGTGAAATTCTTAGATTTGTTAAAGACGNAN-CTNCTGC    SEQ ID NO:62
SG:   ATTTAACTGNNAGAGGTGAAATTCTTAGATTTGTTAAAGNCG-AN-CTNCTGC    SEQ ID NO:63
ST:   ATTTANCTNNNAGAGGTGAAATTCTTAGATTTGTTAAAGACG-AA-CTACTGC    SEQ ID NO:64
TG:   ATTTAACTGTCAGAGGTGAAATTCTTAGATTTGTTAAAGACG-A-CCTACTGC    SEQ ID NO:65
ET:   ATTTAACTGNNAGAGGTGAAATTCTTAGATTTGTTAAAGACG-A--CTACTGC    SEQ ID NO:66
CR:   ATTTAACAGTCAGAGGTGAAATTCTTGAGTTTGTTAAAGACA-AA-CTAATGC    SEQ ID NO:67
```

Figure 1D

```
POS=2181
SN:  GAAAGCATTTGCCAAAGATGTTTTCATTAATCAAGAACGAAAGTTAGGGGCTC    SEQ ID NO:68
SM:  GAAAGCATTTGCCAAAGATGTTTTCATTAATCAAGAACGAAAGTTAGGGGCTC    SEQ ID NO:69
SCA: GAAAGCATTTGCCAAAGATGTTTTCATTAATCAAGAACGAAAGTTAGGGGCTC    SEQ ID NO:70
SA:  GAAAGCATTTGCCAAAGATGTTTTCATTAATCAAGAACGAAAGNNNGGNCTC     SEQ ID NO:71
SCR: GAAAGCATTTGCCAAAGATGTTTTCATTNATCAAGAACGAAAGTNNGGNCTC     SEQ ID NO:72
SG:  GAAAGCATTTGCCAAAGATGTTTTCATTAATCAAGAACGAAAGTTAGGGNCTN    SEQ ID NO:73
ST:  GAAAGCATTTGCCAAAGATGTTTTCATTAATCAAGAACGAAAGTTAGGGGCTC    SEQ ID NO:74
TG:  GAAAGCATTTGCCAAAGATGTTTTCATTAATCAAGAACGAAAGTTNGGGNCTN    SEQ ID NO:75
ET:  GAAAGCATTTGCCAAGGATGTTTTCATTAATCAAGACCGACAGTAGGGGCTC     SEQ ID NO:76
CR:  GAAAGCATTTGCCAAGGATNTTTTCATTAATCAAGANNGAAAGTTAGGGGATC    SEQ ID NO:77

POS=2263
SN:  GAAGACGATCAGATACCGTCGTAGTCTTAACCATAAACTATGCCGA-CTAGAG    SEQ ID NO:78
SM:  GAAGACGATCAGATACCGTCGTAGTCTTAACCATAAACTATGCCGA-CTAGAG    SEQ ID NO:79
SCA: GAAGNCGATCAGATACCGTCGTAGTCTTAACCATAAACTATGCCGA-CTAGAG    SEQ ID NO:80
SA:  GAAG-CGATCAGATACCGTCGTAGTCTTAACCATAAACTATGCCGA-CTAGAG    SEQ ID NO:81
SCR: GNAGNCGATCNGNTNNCGTCGTAGTCNTANCCATNNACTATGNCGA-CTAGAG    SEQ ID NO:82
SG:  GAAGACGATCAGATACCGTCGTAGTCTTAACCATAAACTATGCCGA-CTAGAG    SEQ ID NO:83
ST:  GNAGNCGATNNGATN-CGTNGTNGTCTTNNNCATNNNCTATGNCGANCTNGAG    SEQ ID NO:84
TG:  GAAGACGGATC-GATACCGTCGTAGTCTAATCTCTACCATAAACTATGCCGA-CTAGAG SEQ ID NO:85
ET:  GAAGACGATTAGATACCGTCGTAGTCTTAACCATAAACTATGCCGA-CTAGAG    SEQ ID NO:86
CR:  GAAGACGATCAGATACCGTCGTAGTCTTAACCATAAACTATGCCAA-CTAGAG    SEQ ID NO:87
```

Figure 1E

```
POS=2318
SN:  ATAGGAAAACGTCATCCT--TGACTTCTCCTGCACCTTATGAGAAA-T    SEQ ID NO:88
SM:  ATAGGAAAAAGTCATCCT--TGACTTCTCCTGCACCTTATGAGAAA-T    SEQ ID NO:89
SCA: ATAGGAAAAATGTCATTTGCTGNCNTCTCCTNCACCTTATGAGNNA-T    SEQ ID NO:90
SA:  ATAGGAAAATGTCATTTTGCTGNCTTCTCCTNCNCCTTATGAGAAA-T    SEQ ID NO:91
SCR: ATAGGNAAATNTCATTTT-CTGNCTTCTCCTNCACCTTATGAGAAAGT    SEQ ID NO:92
SG:  ATAGGAAA-TGTCACATTGTTG-CTTCTCC--CACCTTATGAGAAA-T    SEQ ID NO:93
ST:  ATNGGANNATGTNATTTNCTN-CNTCTCCNNCNCCTTATGAGAAA-T     SEQ ID NO:94
TG:  ATAGGAAAACGTCATGCT--TGACTTCTCCTGCACCTTATGAGAAA-T    SEQ ID NO:95
ET:  ATAGGGAAAACGCCTACCT--TGGNNTCTCCTGCACCTCATGAGAAA-T   SEQ ID NO:96
CR:  ATTGGNGNTTGT---TTTCCTTACTCCTTCAGCACCTTATGAGAAA-T    SEQ ID NO:97
```

SARCOCYSTIS NEURONA DIAGNOSTIC PRIMER AND ITS USE IN METHODS OF EQUINE PROTOZOAL MYELOENCEPHALITIS DIAGNOSIS

TECHNICAL FIELD

The present invention relates to an amplification primer and probe which can be used in an in vitro diagnostic test for the presence of S. neurona in equine blood or cerebrospinal fluid.

Sarcocystis neurona is responsible for the equine condition of protozoal myelitis. The amplification primer is seventeen nucleotides in length and complementary to a unique section of the small ribosomal subunit of Sarcocystis neurona, nucleotide positions 1470–1487. The primer has the sequence 5' CCATTCCGGACGCGGGT-3'(SEQ ID NO:1).

BACKGROUND

Equine protozoal myeloencephalitis (EPM) is a treatable, but often fatal, central nervous system (CNS) disease of equids. It has not been reported among horses originating outside the Western hemisphere. Several hundred cases occur in North America annually. Although EPM has been reported in ponies, donkeys and most breeds of horses, the greatest incidence has been among thoroughbreds, standardbreds, and quarter horses.[1] (See references section below.) The disease occurs as a result of infection with Sarcocystis neurona. Merozoites multiply in neurons, leucocytes and vascular endothelial cells of the CNS resulting in perivascular mononuclear cell infiltration and necrosis of the neuropile. Antemortem diagnosis of EPM is difficult.[2] Clinical signs vary dramatically, depending upon the location and severity of CNS lesions. The disease may mimic various neurological disorders of the horse. Clinicopathologic data are frequently of little diagnostic value.

Some methods of diagnosing equine parasitic and other infections are known. For example, U.S. Pat. No. 4,740,456 to Kuhn et al. discloses immunological methods for diagnosing active human neurocysticercosis, including a serum test and a cerebrospinal fluid test. The test involves detecting an antigen or antigens of larval origin, specifically of Taenia solium larva.

U.S. Pat. No. 4,759,927 to Dutta discloses a vaccine against Potomac Horse Fever comprising deactivated E. Risticii as the active agent. The patent also discloses an assay for detecting the presence of E. Risticii antibodies.

U.S. Pat. No. 5,141,925 to Alroy et al. discloses a method for the prophylactic and therapeutic treatment of animals having a parasite able to cause Coccidiosis.

U.S. Pat. No. 5,210,018 to Nuzzolo et al. discloses an immunoenzymatic method for the detection of anti-Plasmodium falciparum-sporozoite antibodies in human blood.

"Evidence for Sarcocystis as the etiologic agent of equine protozoal myeloencephalitis", Simpson et al., J Protozool (UNITED STATES) August 1980, 27 (3) p288–92, discloses the diagnosis of Equine protozoal myeloencephalitis (EPM) in 10 horses. By electron microscopy, schizonts were found in intact host cells of the spinal cords or, more frequently, free in the extracellular spaces. Developmental stages of schizonts differed morphologically, and the late stage of schizogony was characterized by endopolygeny. These findings permitted tentative identification of the protozoan as a Sarcocystis sp. Free merozoites were present in the extracellular spaces or in cells of the spinal cord. Pericytes of capillaries were most frequently parasitized by merozoites, but the cytoplasm of neurons, macrophages, intravascular and tissue neutrophils, and axons of myelinated nerve fibers also contained these organisms. The presence of parasites in the cytoplasm of tissue and circulating neutrophils suggest that this putative Sarcocystis sp. may have a hematogenous phase of infection.

"Immunohistochemical study to demonstrate Sarcocystis neurona in equine protozoal myeloencephalitis", Hamir et al., J. Vet. Diagn. Invest. (UNITED STATES) July 1993, 5 (3) p418–22; discloses a 5-year (1985–1989) retrospective immunohistochemical study was conducted using an avidin-biotin complex (ABC) immunoperoxidase method to demonstrate Sarcocystis neurona in histologically suspect cases of equine protozoal myeloencephalitis (EPM). Primary antibodies against S. neurona and S. cruzi were utilized for the ABC technique. The findings were compared with those from cases in which the organisms were detected by examination of hematoxylin and eosin (HE)-stained neuronal sections. HE-stained sections detected the presence of the organisms in 20% of the suspect cases; whereas the ABC technique confirmed the presence of S. neurona in 51% and 67% of the cases by S. neurona and S. cruzi antibodies, respectively. A review of clinical case histories showed that 21/47 (45%) of the EPM horses with parasites in the tissue sections had prior treatment with antiprotozoal drugs and/or steroids. Using the test results of S. neurona and S. cruzi as a standard reference, HE test sensitivity based on examination of up to 30 neuronal sections per case was only 25%, and test specificity was 91%.

"Equine protozoal myeloencephalitis: Antigen analysis of cultured Sarcocystis neurona merozoites", Granstrom et al., J. Vet. Diagn. Invest. (UNITED STATES) January 1993, 5(1) p 88–90; discloses antigens of cultured Sarcocystis neurona merozoites were examined using immunoblot analysis. Blotted proteins were probed with S. cruzi, S. muris, and S. neurona antisera produced in rabbits, S. fayeri (pre- and post-infection) and S. neurona (pre- and post-inoculation) sera produced in horses, immune sera from 7 histologically confirmed cases of equine protozoal myeloencephalitis (EPM), and pre-suckle serum from a newborn foal. Eight proteins, 70, 24, 23.5, 22.5, 13, 11, 10.5, and 10 Kd, were detected only by S. neurona antiserum and/or immune serum from EPM-affected horses. Equine sera were titered by the indirect immunofluorescent antibody (IFA) method using air-dried, cultured S. neurona merozoites. Anti-Sarcocystis IFA titers were found in horses with or without EPM. Serum titers did not correspond to the number of specific bands recognized on immunoblots.

"A five year (1985–1989) retrospective study of equine neurological diseases with special reference to rabies", Hamir et al., J. Comp. Pathol. (ENGLAND) May 1992, 106 (4) p411–21; discloses a retrospective study of horses necropsied between 1985 and 1989 at a diagnostic laboratory of a veterinary school in North America is documented. In this investigation over 20 per cent of the horses had clinical neurological signs. Equine protozoal myeloencephalitis (caused by Sarcocystis neurona) and cervical stenotic myelopathy (wobbler syndrome) were the most common of these disorders. However, only four cases of equine rabies were diagnosed during the 5-year study. The gross microscopical and immunohistochemical findings from these rabies-positive horses are documented. Immunoperoxidase tests for detection of rabies antigen in another 35 horses with non-specific encephalitis/encephalopathydid not reveal any positive cases. Based on this investigation, it appears that immunoperoxidase is a valid method for diagnosis of rabies when fresh tissues are not available for the fluorescent antibody test.

"Characterization of *Sarcocystis neurona* from a thoroughbred with equine protozoal myeloencephalitis", Bowman et al., appears in Cornell Vet. 1992, April 82(2):115, Cornell Vet. (UNITED STATES) January 1992, 82 (1) p41–52 and discloses morphological information for syntype material of the etiologic agent of equine protozoal myeloencephalitis, *Sarcocystis neurona*. A clinical description of the horse from which the organism was isolated and the methodology used to immunosuppress the horse in an attempt to increase parasite numbers are also given. The description includes microscopic details observed both with light and transmission electron microscopy. Mainly stages from tissue are illustrated, but information is also presented on the development of the organism after inoculation on to monolayers of bovine monocytes. It is believed that the large numbers of organisms observed in this horse were due to its having not received prior treatment with trimethoprimsulphonamide and the large amounts of corticosteroids that were administered in order to facilitate isolation of the pathogen.

"*Sarcocystis neurona* n. sp. (Protozoa: Apicomplexa), the etiologic agent of equine protozoal myeloencephalitis", Dubey et al., J Parasitol (UNITED STATES) April 1991, 77 (2) p212–8; discloses *Sarcocystis neurona* n. sp. is proposed for the apicomplexan taxon associated with myeloencephalitis in horses. Only asexual stages of this parasite presently are known, and they are found within neuronal cells and leukocytes of the brain and spinal cord. The parasite is located in the host cell cytoplasm, does not have a parasitophorous vacuole, and divides by endopolygeny. Schizonts are 5–35 microns ×5–20 microns and contain 4–40 merozoites arranged in a rosette around a prominent residual body. Merozoites are approximately 4×1 micron, have a central nucleus, and lack rhoptries. Schizonts and merozoites react with *Sarcocystis cruzi* antiserum but not with *Caryospora bigenetica. Toxoplasma gondii, Hammondia hammondi*, or *Neospora caninum* antisera in an immunohistochemical test.

"Equine protozoal myeloencephalitis", Madigan et al., Vet. Clin. North Am. Equine Pract. (UNITED STATES) August 1987, 3 (2) p397–403; discloses Equine protozoal myeloencephalitis (EPM) is a disease that produces neurologic signs of brain or spinal cord dysfunction. The causative organism is believed to be a Sarcocystis species of protozoa. A definitive diagnosis can only be made on histopathology of affected spinal cord or brain. No preventive measures or documented treatment is available at this time for suspected cases of EPM.

Currently the only method of antemortem diagnosis of equine sarcocystis (EPM) is by Western Blot, which detects the presence of antibodies against *S. neurona*. Blood contamination of the spinal fluid, or loss of integrity of the blood-brain barrier may result in false positive tests. A DNA based test according to the present invention circumvents these problems. Recently, progress has been made in the development of serological methods for EPM diagnosis. The availability of cultured merozoites has made it possible to detect *S. neurona*-specific antibodies in serum and cerebrospinal fluid of affected horses.[3] Immunoblot analysis of these samples distinguishes between exposure to *S. neurona* and *S. fayeri* a common, non-pathogenic, coccidia of the horse. Previous serologic tests relied on *S. cruzi* bradyzoite antigen which only detected antibodies to shared or cross-reactive Sarcocystis spp. epitopes. Preliminary immunoblot screening of several groups of horses in central Kentucky indicated that many horses are exposed while few develop clinical signs .[4] At present, there is no method to directly detect and differentiate *S. neurona* from non-pathogenic Sarcocystis in live animals.

There is a need in the art for a diagnostic method of detecting Equine protozoal myeloencephalitis (EPM). The primer/probe of the present invention provides the first diagnostic primer for the diagnosis of Equine protozoal myeloencephalitis (EPM) caused by the parasite *Sarcocysitis neurona.*

DISCLOSURE OF THE INVENTION

The present invention provides an amplification primer/probe which can be used in an in vitro diagnostic test for the presence of *S. neurona* in equine blood or cerebrospinal fluid. *Sarcocystis neurona* is responsible for the equine condition of protozoal myelitis.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

BRIEF DESCRIPTION OF DRAWINGS

FIGS. 1(A)–(E) shows the relatedness of a 450 nt sequence from SRSU of *S. neurona* when compared to *S. muris, S. gigantea, T. gondii, S. capicanis, S. arieticanis, S. cruzi, S. tenella, E. tenella* and *C. parvum* by comparison of sequences from the small ribosomal subunit of each.

FIG. 2 shows a phylogenic tree depicting the relatedness of the complete gene sequence (1806 nt) of SRSU of *S. neurona* when compared to *S. muris, S. gigantea, T. gondii, S. capicanis, S. arieticanis, S. cruzi, S. tenella, E. tenella* and *C. parvum* by comparison of sequences from the small ribosomal subunit of each.

FIG. 3 shows a gel showing efficacy of the probe according to the present invention.

DESCRIPTION OF THE INVENTION

*Sarcocystis neurona* is the etiologic agent of Equine protozoal myeloencephalitis (EPM) which was isolated and described in 1991. There are limited means available for antemortem detection of this protozoan in horses, and the life cycle and mode of transmission and pathogenesis of this disease remain unknown.

The gene sequence of the *Sarcocystis neurona* small ribosomal subunit (SRSU) was determined using polymerase chain reaction techniques and Sanger sequencing methods. The SRSU gene was found to be 1806 nucleotides (nt) in length and have a G/C content of 46%. The small ribosomal subunit gene is an ideal molecular marker because it contains both sequences which are highly conserved among species and sequences which are variable. Variable regions are used to determine genetic relatedness of protozoal organisms. For example, FIG. 1 shows the relatedness of a 450 nt sequence from SRSU of *S. neurona* when compared to *S. muris, S. gigantea, T. gondii, S. capicanis, S. arieticanis, S. cruzi, S. tenella, E. tenella* and *C. parvum* by comparison of sequences from the small ribosomal subunit of each. FIG. 2 shows a phylogenic tree depicting the relatedness of the complete gene sequence (1806 nt) of SRSU of *S. neurona* when compared to *S. muris, S. gigantea, T. gondii, S. capicanis, S. arieticanis, S. cruzi, S. tenella, E. tenella* and *C. parvum* by comparison of sequences from the small ribosomal subunit of each.

The present inventors have isolated an rDNA sequence which can be used as a species-specific diagnostic probe and primer for *Sarcocystis neurona*. The methodology for isolating the rDNA probe is set forth below.

EXAMPLE 1

Parasite Isolation and DNA Preparation

Merozoites of *S. neurona* (fifth isolate, strain SN5) were cultured in vitro from the spinal cord of an infected horse which was necropsied at the University of Kentucky Livestock Disease Diagnostic Center. The parasite was maintained in tissue culture in bovine monocytes (provided by C. A. Speer, Montana State University) supplemented with 10% neonatal bovine serum (Biowhittaker, Walkersville, Md.) in RPMI 1640 media (Biowhittaker, Walkersville, Md.). Culture media were removed from the culture vials, centrifuged at 800×G for 20 min to pellet the cells, then resuspended in Hank's balanced salt solution (Biowhittaker, Walkersville, Md.). The suspension of parasites and bovine monocytes was layered above 1 ml of Percoll (Sigma, St. Louis, Mo.) at a specific gravity of 1.070, and centrifuged at 400×G for 20 min. Merozoites were found in the pellet, while the bovine monocytes were found at the Hank's balanced salt solution-percoll interface.

Approximately $5\times10^6$ merozoites were washed in 1 ml phosphate-buffered saline (PBS), then resuspended in 20 $\mu$l PBS, and 200 $\mu$l of 50% Chelex-100 (Bio-Rad, Richmond, Calif.). *S. neurona* DNA was released by boiling this suspension for 5 min. The sample was subsequently quenched on ice for 5 min, and centrifuged. This supernatant was used in the polymerase chain reaction (PCR) for the amplification of the small ribosomal subunit gene.

DNA Amplification

The PCR (Saiki et al., 1988) was performed using eukaryotic specific universal amplification primers developed by Medlin et al., (1988). The described amplification protocol was modified to optimize DNA yield. The "hot start" technique (Mullis, 1991) was employed to limit mispriming at the onset of the reaction. Amplification primers, $MgCl_2$, and dNTP in PCR buffer (10 mM Tris-HCl, pH=8.3, 50 mM KCl) were placed in 0.5 ml microcentrifuge tubes, and overlaid with 40 $\mu$l paraffin wax. Ten $\mu$l of Chelex supernatant and Taq polymerase (1.25 U, Amplitaq, Perkin-Elmer, Norwalk, Conn.) in PCR buffer were overlaid on the wax, and the microcentrifuge tubes were placed in a thermocycler (Perkin-Elmer, Norwalk, Conn.). The final concentrations of reagents were 0.5 $\mu$M of each primer, 2 mM $MgCl_2$ and 500 $\mu$M of each deoxynucleotide.

Denaturation of the DNA in the reactions was accomplished by heating to 94° C. for 1 min. The annealing temperature was 55° C. for 1 min, and the elongation temperature was 72° C. for 2 min. These sequential incubations were repeated for 5 cycles, and then 30 additional cycles were performed at the same conditions, with the exception of an annealing temperature of 50° C. for 1 min. The final primer extension was continued for 7 min to permit complete elongation of all amplified product.

Cloning into a pT7Blue Vector

The PCR product was purified by ultrafiltration (Krowczynska and Henderson, 1992) using microcon-100 microconcentrators (Amicon, Beverly, Mass.). The amplified product was directly ligated into a pT7Blue vector (Novagen, Madison, Wis.) and transformed according to the recommendations of the manufacturer. Transformed cells were selected by culturing on LB agar plates containing 50 $\mu$g/ml ampicillin and 15 $\mu$g/ml tetracycline. Colonies containing PCR product insert were selected using blue/white screening, by the addition of 40 $\mu$l of 20 mg/ml X-gal in dimethyl formamide, and 4 $\mu$l 200 mg/ml IPTG per 100 mm plate. Plates were incubated for 12 to 24 hours (Sambrook, Fritsch and Maniatis, 1989). White colonies were screened for insert by PCR. Individual colonies were scraped from the plate, and diluted in 20 $\mu$l of sterile water in 1.5 ml microcentrifuge tubes. These were boiled for 2 min to release plasmid DNA, and 10 $\mu$l of supernatant was used in the PCR protocol described above. Twelve positive clones were identified in this manner, and two were arbitrarily chosen for sequencing.

Dideoxynucleotide Sequencing and Analysis

Small scale plasmid purifications were performed for two positive clones, by a protocol modified from Sambrook et al. (1989). Alkaline denaturation of these plasmid solutions was performed to yield single stranded template. Sanger sequencing reactions were performed using these templates. Primers used for sequencing included primers complementary to regions of the vector flanking the insert, and also synthetic primers complementary to conserved regions of the eukaryotic small ribosomal subunit gene (Elwood et al., 1985). Additional internal primers (840F: 5' GGATTTCGGT TCTATTTTGT TGG 3'(SEQ ID NO:2, and 1055R: 5' GTTTCAGCCT TGCGACCAT 3'(SEQ ID NO:3) were designed from the partial sequence to determine the complete sequence.

The complete gene sequence of the small ribosomal subunit of *S. neurona* has 1806 nt. A specific 450 nt sequence fragment from SRSU of *S. neurona* was also obtained and is disclosed.

EXAMPLE 2

Various amplification primers for the SRSU gene which are species-specific for *Sarcocystis neurona* were tested. The amplification primer for *Sarcocystis neurona* SRSU with species specificity is seventeen nucleotides in length and complementary to a unique section of the small ribosomal subunit of *Sarcocystis neurona*. The unique amplification primer encompasses nucleotide positions 1470–1487. The primer has the sequence:

5'-CCATTCCGGACGCGGGT- 3'(SEQ ID NO:1). The primer/probe may be modified at the 3' end by adding 1–5 nucleotides, such that the primer/probe maintains the function of the original probe and hybridizes specifically to *Sarcocystis neurona* small ribosomal subunit.

1470R Ampli. Primer: 5' CCATTCCGGACGCGGGT 3'(SEQ ID NO:1) MW=5267

The 1470 R primer can be coupled to a detectable label and used as a diagnostic probe for the detection of *Sarcocytis neurona*. The detectable label may be selected from the group consisting of chromophores, fluorophores, chemiluminescent materials and radioisotopes. Alternatively the primer may be used as a PCR primer as set forth below.

EXAMPLE 3

The advent of DNA based diagnostic assays has facilitated rapid, accurate identification of micro-organisms through the use of species-specific nucleotide sequences. Generally, DNA probes have been developed from unique gene or intergenic sequences for DNA probes, or from repetitive elements. In addition, development of the polymerase chain reaction (PCR) has greatly increased the speed at which new diagnostic assays can be developed.[5] The time required to construct DNA libraries or clone specific DNA fragments has been reduced considerably by the ability to directly amplify the desired DNA region.

The methodology for the nested polymerase chain reaction (PCR) procedure used to conduct the diagnostic assay according to the present invention is set forth below.

Nested PCR Diagnostic Method

I. Required Reagents/Supplies/Equipment

A. Supplies:

Sterile 1.5 ml. microfuge tubes

Sterile 0.5 ml. microfuge tubes
Blue (first stage)
Yellow (second stage)

PCR wax beads (created by dropping 30 μl hot paraffin wax on tin foil)

forceps for wax beads 1.5 and 0.5 ml tube racks styrofoam ice cooler ice dedicated 1000 μl, 200 μl pipetman pipettors sterile, plugged tips for 1000 μl and 20 μl Thermocycler (48 reactions)

Dedicated microcentrifuge

B. Reagents:

Millipore water, sterilized and in 1 ml. aliquots (store in freezer)

DMSO, in 1 ml. aliquots (store away from light in box)

Perkin-Elmer 10×PCR buffer

Perkin-Elmer dNTPs, 10 mM per each, mixed together to form a single dNTP mixture containing 2.5 mM each nucleotide Perkin-Elmer $Mg_2Cl$, 25 mM Primer 1470R (unique primer, reverse primer, first stage), 10 mM, 5' CCATTCCGGACGCGGGT- 3'(SEQ ID NO:1) Primer 1184F (forward primer, first stage), 10 mM 5' CCAGGCGTGGAGCTGCG-3'(SEQ ID NO:4) Primer 1055F (forward primer, second stage), 10 mM 5' GGTGGTGGTGCATGGCCG-3'(SEQ ID NO:5) Primer 1475R (reverse primer, second stage), 10 mM 5' GCGCGTGGCCCAGAAC-3'(SEQ ID NO:6) (Primers may be synthesized on Applied Biosystems DNA synthesizer)

Ethidium Bromide

DNA 100 bp ladder

II. First Stage Reaction:

A. The nested PCR reaction with hot start technique is set up in several stages. First, the hot start technique requires a lower reaction including the primers and dNTPs in PCR buffer. The wax is overlaid and melted over the lower reaction mixture. The upper reaction containing the DNA template (in this case, cerebrospinal fluid (CSF)) and Taq polymerase are placed in PCR buffer on top of the wax. A drop (20 to 40 μl) of sterile mineral oil is put on top to prevent excessive evaporation from the upper reaction mixture. The entire tube is then spun briefly to collect the fluid at the bottom of the tube.

| B. Lower Reaction Mixture | | | |
|---|---|---|---|
| Reagents | 'X 1' (μl) | Concentrations | 'X 50' (μl) |
| P1184F | 5.00 | 1 mM | 250.00 |
| P1470R | 5.00 | 1 mM | 250.00 |
| $MgCl_2$ | 8.00 | 4 mM | 400.00 |
| dNTPs | 4.00 | 1 mM | 200.00 |
| 10 × PCRB (+$MgCl_2$) | 2.50 | 1 X | 125.00 |
| DMSO | 2.50 | 5% | 125.00 |
| $mpH_2O$ | 3.00 | — | 150.00 |
| Reaction Volume | 30.00 | — | 1500.00 | f = forward primer;
r = reverse primer

The lower reaction mixture is made up on 50 reaction quantities in a 1.5 ml microcentrifuge tube. This mixture (labelled "#1", and dated) may be frozen for at least 1 month safely. When the nested reaction is to be performed, the tube is slowly thawed, mixed by pipetting up and down, then 30.0 μl aliquots are placed into 48 blue 0.5 ml microfuge tubes. A wax bead (PCR gem) is placed in the tube over the solution. The tubes are placed in the therinocycler at 80° C. for 5 minutes to melt the wax, and then cooled to 4° C. to harden the wax. Alternatively, the tubes may be placed in a water bath (>65° C.) for about 5–10 minutes, then removed carefully and placed in a refrigerator for a few minutes.

| C. Upper Reaction Mixture | | | |
|---|---|---|---|
| Reagents | 'X 1' (μl) | Concentrations | "X 50' (μl) |
| $mpH_2O$ | 7.25 | — | 362.50 |
| 10 × PCRB | 2.50 | 1 X | 125.00 |
| Taq | 0.25 | — | 12.50 |
| Template | 10.00 | — | — |
| Reaction Volume | 20.00 | — | 500.00 |

The upper reaction mixture must be made up fresh, and chilled in ice throughout the procedure. The reagents must be added to the upper reaction mixture in order, so that the PCR buffer is in the solution before the Taq is added. The upper reaction mixture, not including the DNA template (CSF) is made up and then 10 μl aliquots are placed over the wax into the blue microcentrifuge tubes containing the lower reaction.

Forty clinical samples can be tested per run, with seven water controls and a positive *S. neurona* control. Preferably, about ten μl of each clinical cerebrospinal fluid (CSF) is placed into a tube, and mixed with the upper reaction mixture by pipetting up and down. Care must be taken to avoid cross-contamination. The tubes are numbered 1 to 48, with numbers 1, 8, 15, 22, 29, 38, and 47 as water, or reagent controls. These should be done in order for internal control. Number 48 is the positive *S. neurona* control. The reagent controls will have the same water tube which was used for the reaction setup as the "DNA template" to control for the accidental carryover of PCR product into this water. Each reaction tube should then be overlaid with a drop of sterile mineral oil to avoid evaporation.

D. Thermal-cycle Profile

The tubes are placed in the thermal-cycler, and the amplification protocol follows:

| Cycle | Temperature | Duration |
|---|---|---|
| 1 | Denaturing temp: 92 C. | 2 min |
|  | Annealing temp: 58 C. | 30 min |
|  | Extension temp: 74 C. | 1 min |
| 2–6 | Denaturing temp: 92 C. | 30 sec |
|  | Annealing temp: 58 C. | 30 sec |
|  | Extension temp: 74 C. | 1 min |
| 7–31 | Denaturing temp: 92 C. | 30 sec |
|  | Annealing temp: 54 C. | 30 sec |
|  | Extension temp: 74 C. | 1 min |
| 32 | Denaturing temp: 92 C. | 30 sec |
|  | Annealing temp: 54 C. | 30 sec |
|  | Extension temp: 74 C. | 7 min |
| 33 | Soak temp: 4 C. | Until removed |

Samples are removed, and the wax is pierced with a sterile pipette tip. Then, 10 $\mu$l of the product is used as the DNA template for the second stage reaction.

III. Second Stage Reaction

A. It is critical that no PCR carryover occur, and therefore, the entire procedure is done in a UV-clean area. Addition of the PCR product from the first reaction, is performed in a different area, so as not to risk contamination of "clean" area.

B. Lower Reaction Mixture

| Reagents | 'X 1' ($\mu$l) | Concentrations | 'X 50" ($\mu$l) |
|---|---|---|---|
| P1055F | 5.00 | 1 mM | 250.00 |
| P1475R | 5.00 | 1 mM | 250.00 |
| MgCl$_2$ | 4.00 | 1 mM | 200.00 |
| dNTPs | 4.50 | 1 mM | 200.00 |
| 10 × PCRB | 2.50 | 1 X | 125.00 |
| mpH$_2$O | 8.50 | — | 425.00 |
| Reaction Volume | 30.00 | — | 1500.00 |

The lower reaction mixture is made up in 50 reaction quantities in a 1.5 ml microcentrifuge tube. This mixture (labelled "#2", and dated) may be frozen for at least 1 month safely.

When the nested reaction is to be performed, the tube is slowly thawed, mixed by pipetting up and down, then 30.0 $\mu$l aliquots are placed into 48 yellow 0.5 ml microfuge tubes. A wax bead (PCR gen) is placed in the tube over the solution. The tubes are placed in the thermocycler at 80° C. for 5 minutes to melt the wax, and then cooled to 4° C. to harden the wax. Alternatively, the tubes may be placed in a water bath (>65° C.) for about 5–10 minutes, then removed carefully and placed in a refrigerator for a few minutes.

C. Upper Reaction Mixture

| Reagents | 'X 1' ($\mu$l) | Concentrations | 'X 50' ($\mu$l) |
|---|---|---|---|
| mpH$_2$O | 7.25 | — | 362.50 |
| 10 × PCRB | 2.50 | 1 X | 125.00 |
| Taq | 0.25 | — | 12.50 |
| Template | 10.00 | — | — |
| Reaction Volume | 20.00 | — | 500.00 |

The upper reaction mixture must be made up fresh, and chilled in ice throughout the procedure. The reagents are added to the upper reaction mixture in order, so that the PCR buffer is in the solution before the Taq is added. The upper reaction mixture, not including the DNA template (CSF) is made up and then 10 $\mu$l aliquots are placed over the wax into the yellow microcentrifuge tubes containing the lower reaction.

Ten $\mu$l of each blue tube (first stage) reaction is placed into a tube, and mixed with the upper reaction mixture by pipetting up and down. Care must be taken to avoid cross-contamination. The tubes are numbered 1 to 48, to correspond to the same tubes from which product will be used for template. Each reaction tube is then overlaid with a drop of sterile mineral oil to avoid evaporation.

D. Thermal-cycle Profile

The tubes are placed in the thermal-cycler, and the amplification protocol follows:

| Cycle | Temperature | Duration |
|---|---|---|
| 1 | Denaturing temp: 92 C. | 2 min |
|  | Annealing temp: 57 C. | 30 min |
|  | Extension temp: 74 C. | 1 min |
| 2–6 | Denaturing temp: 92 C. | 30 sec |
|  | Annealing temp: 57 C. | 30 sec |
|  | Extension temp: 74 C. | 1 min |
| 7–31 | Denaturing temp: 92 C. | 30 sec |
|  | Annealing temp: 53 C. | 30 sec |
|  | Extension temp: 74 C. | 1 min |
| 32 | Denaturing temp: 92 C. | 30 sec |
|  | Annealing temp: 53 C. | 30 sec |
|  | Extension temp: 74 C. | 7 min |
| 33 | Soak temp: 4 C. | Until removed |

Samples are removed, and the wax is pierced with a sterile pipette tip. Then, the PCR product is run out on a horizontal gel apparatus in a TAE 1% agarose gel at 100 V for about 2–3 hours. The band should be about 250 bp in length when compared to the DNA 100 bp latter. Presence of a band is determined by EtBr staining. Stained band indicates *Sarcocystis neurona* is present in specimen.

In an alternative embodiment, the conditions for PCR using the species specific primer of the present invention follow: PCR Conditions Lower reaction mix

|  | X1 | X5 | X1 | X5 | X1 | X5 |
|---|---|---|---|---|---|---|
| 1055F | 2.5 | 12.5 | 2.5 | 12.5 | 2.5 | 12.5 |
| 1470R | 2.5 | 12.5 | 2.5 | 12.5 | 2.5 | 12.5 |
| MgCl$_2$ | 3.0 | 30.0 | 4.0 | 20.0 | 8.0 | 40.0 |
| dNTP | 4.0 | 20.0 | 4.0 | 20.0 | 4.0 | 20.0 |
| PCRB | 2.5 | 12.5 | 2.5 | 12.5 | 2.5 | 12.5 |
| DMSO | 5.0 | 25.0 | 5.0 | 25.0 | 5.0 | 25.0 |
| dH$_2$O | 7.5 | 37.5 | 9.5 | 47.5 | 5.5 | 27.5 |
| Mix | 1(N) | | 2(B) | | 3(G) | |

| Upper Rxn | Mix | X1 | X13 |
|---|---|---|---|
| Taq |  | .25 | 3.25 |
| Template |  | 1 $\mu$l | 13 |
| PCRB |  | 2.5 | 32.5 |
| dH$_2$O |  | 16.25 | 211.25 |

Figure 3:
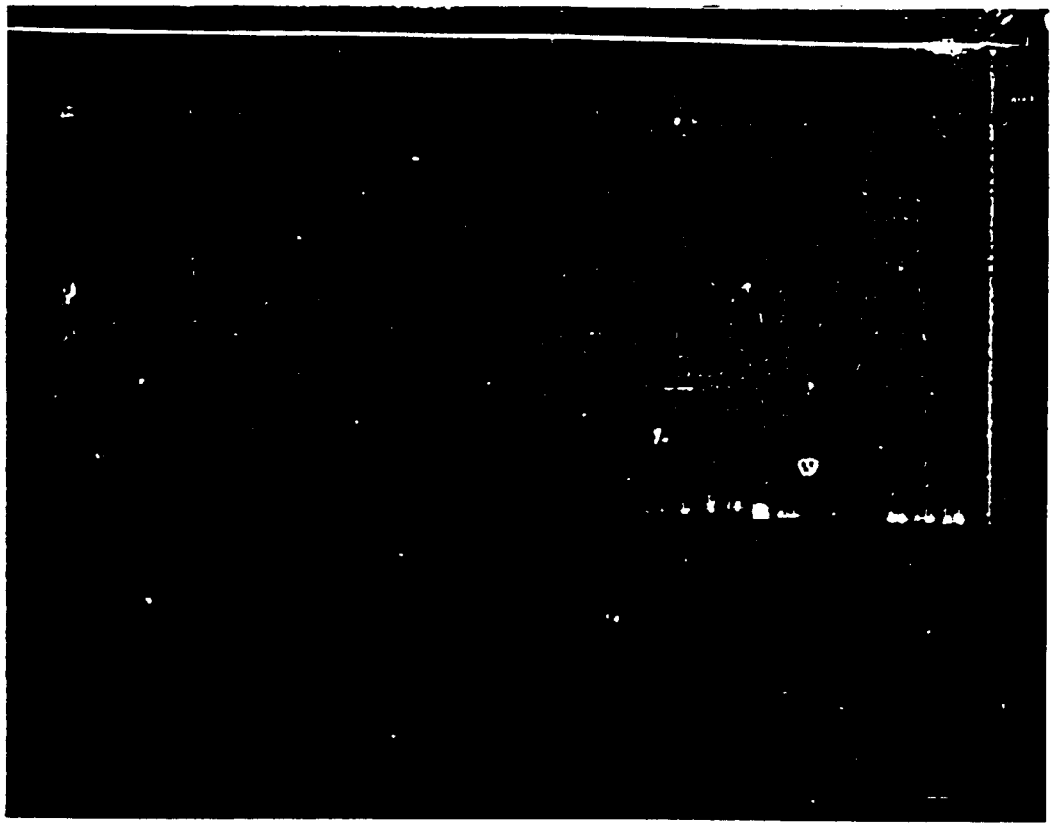

FIG. 3, shows a gel showing efficacy of the probe according to the present invention. A detailed description of the gel lanes in FIG. 3 follow:

| Lanes | |
|---|---|
| 1 | 100 bp Ladder |
| 2 | 1.0 µl pr, 2 mM MgCl$_2$, 10 ng DNA Templ. |
| 3 | 1.0 µl pr, 2 mM MgCl$_2$, 40 ng DNA Templ. |
| 4 | 1.0 µl pr, 2 mM MgCl$_2$, 80 ng DNA Templ. |
| 5 | 1.0 µl pr, 3 mM MgCl$_2$, 10 DNA |
| *6 | 1.0 µl pr, 3 mM MgCl$_2$, 40 DNA |
| *7 | 1.0 µl pr, 3 mM MgCl$_2$, 80 DNA |
| *8 | 2.5 µl pr, 1 mM MgCl$_2$, 10 |
| *9 | 2.5 µl pr, 1 mM MgCl$_2$, 40 |
| *10 | 2.5 µl pr, 1 mM MgCl$_2$, 80 |
| 11 | 2.5 µl pr, 2 mM MgCl$_2$, 10 |
| 12 | 2.5 µl pr, 2 mM MgCl$_2$, 40 |
| 13 | 2.5 µl pr, 2 mM MgCl$_2$, 80 |
| 14 | 2.5 µl pr, 3 mM MgCl$_2$, 10 |
| 15 | 2.5 µl pr, 3 mM MgCl$_2$, 40 |
| *16 | 2.5 µl pr, 3 mM MgCl$_2$, 80 |
| *17 | 3.0 µl pr, 2 mM MgCl$_2$, 10 |
| 18 | 3.0 µl pr, 2 mM MgCl$_2$, 40 |
| 19 | 3.0 µl pr, 2 mM MgCl$_2$, 80 |
| 20 | 1.0 pr, 2 mM MgCl$_2$, DMSO, 10 |
| 21 | 1.0 pr, 2 mM MgCl$_2$, DMSO, 40 |
| 22 | 1.0 pr, 2 mM MgCl$_2$, DMSO, 80 |
| *23 | 2.0 pr, 3 mM MgCl$_2$, DMSO, 10 |
| *24 | 2.0 pr, 3 mM MgCl$_2$, DMSO, 40 |
| *25 | 2.0 pr, 3 mM MgCl$_2$, DMSO, 80 |
| *26 | 2.5 pr, 1 mM MgCl$_2$, DMSO, 10 |
| **27 | 2.5 pr, 1 mM MgCl$_2$, DMSO, 40 |
| *28 | 2.5 pr, 1 mM MgCl$_2$, DMSO, 80 |
| *29 | 2.5 pr, 2 mM MgCl$_2$, DMSO, 10 |
| *30 | 2.5 pr, 2 mM MgCl$_2$, DMSO, 40 |
| *31 | 2.5 pr, 2 mM MgCl$_2$, DMSO, 80 |
| **32 | 2.5 pr, 3 mM MgCl$_2$, DMSO, 10 |
| **33 | 2.5 pr, 3 mM MgCl$_2$, DMSO, 40 |
| **34 | 2.5 pr, 3 mM MgCl$_2$, DMSO, 80. |

(*—marks (+) lane,
**—marks excellent probe)

EXAMPLE 4

In an alternative embodiment a RAPD assay may be used to detect *Sarcocystis neurona*. Unlike standard PCR, the random amplified polymorphic DNA (RAPD) assays is a procedure which amplifies DNA fragments without the use of specific primers, thus circumventing the need for nucleotide sequence information and specific primer design.[6,7] These random DNA fragments are often polymorphic among species and isolates, behave as dominant alleles, and are inherited in a Mendelian fashion. Therefore, not only can they be used in the same manner as restriction fragment length polymorphic (RFLP) markers to characterize an organism's genome through genetic mapping, but also as a means to differentiate species or isolates.[8,9]

The present inventors utilize the RAPD assay as a means to differentiate four isolates of S. neurona from other coccidial species and have isolated a short DNA fragment which is useful as a specific DNA probe for *S. neurona*. Four isolates of *Sarcocystis neurona* from horses with equine protozoal myeloencephalitis and eight species of coccidia from the genera Sarcocystis, Toxoplasma or Eimeria were differentiated using the random amplified polymorphic DNA (RAPD) assay. A single, common 550-bp DNA fragment was amplified from the DNA of each *S. neurona* isolate using a 16 nucleotide universal primer (TGF):

5'-GCACGAACGCGCCACAAA-3'(SEQ ID NO:7).

Cross-hybridization analysis among *S. neurona* isolates showed that DNA fragments had at least partial sequence homology. The primer generated several DNA fragments, including a 550-bp DNA fragment, from *S. cruzi, Eimeria falciformis, E. neischulzi, E. ahsata* and *E. bovis*. DNA hybridization analyses indicated no sequence homology between these fragments and the 550-bp fragment generated from *S. neurona*. The *S. neurona* 550-bp DNA fragment also did not hybridize with genomic blots of various other coccidia. These results evidence that the *S. neurona* DNA fragment 550 bp fragment is also a species-specific probe for this parasite.

Diagnostic Assay

Four geographic isolates of *S. neurona* were used; SN 2 and SN 4 from California,[10,11] Sn 3 from Panama[12] and Sn 5 from Kentucky. Organisms were isolated from gross spinal cord lesions and grown in bovine monocyte (M617) cell cultures as originally described by Dubey et al.[13] Merozoites were isolated and purified from cultures as previously described by Granstrom et al.[3] DNA from *S. neurona, S. cruzi, S. campestris, Toxoplasma gondii* or bovine monocytes was extracted using proteinase K digestion and phenol/chloroform extraction as described by Gajadhar et al.[14] DNA was extracted from *Eimeria tenella, E. falciformis, E. nieschulzi, E. ahsata* or *E. bovis* as outlined previously.[8]

Each RAPD assay consisted of a 25-µl reaction volume which contained approximately 50 ng of DNA from each species or geographic isolate, 1.5 OU Taq DNA polymerase (Promega, Madison, Wis., USA) in 50 mM KCl, 10 mM Tris-HCl, pH 9.0, 3.0 mM MgCl$_2$, 0.01% gelatin, 0.1% Triton X-100, 0.4 µM primer (TGF; 5'-GCACGAACGCGCCACAAA-3'(SEQ ID NO:7) and 200 µM of each dNTP.

The samples were overlaid with 25 µl of mineral oil and preincubated for 10 min at 94° C. in a DNA Thermal Cycler model 480 (Perkin-Elmer Cetus Corporation, Norwalk, Conn., USA). This was followed by 40 cycles of 94° C. for 30 s, 38° C. for 30 s, 72° C. for 45 s, as suggested by Yu and Pauls.[15] After completion of the thermal cycling reaction, a final 10-min incubation at 72° C. was performed.

DNA fragments generated by PCR were separated by electrophoresis on 1.2% agarose gels in borate buffer and visualized by staining with ethidium bromide.[16] DNA fragments unique to *S. neurona* were isolated from agarose gels by band excision and purified using Quiex (Qiagen, Chatsworth, Calif., USA). Putative DNA probe fragments were labelled with [alpha-$^{32}$P] dATP using *Escherichia coli* DNA polymerase 1 as described by Rigby et al.[17]

The putative DNA probe fragments were analyzed using standard hybridization conditions.[16] DNA fragments were applied to Zeta probe GT membranes (BioRad, Hercules, Calif.) and baked in vacuo at 80° C. for 2 h. Genomic DNA from *S. cruzi, S. campestris, T. gondii, E. nieschulzi, E. ahsata, E. vermiformis, E. coli* or bovine monocytes were digested with Pst 1 at 37° C. for 2 h. The resulting DNA fragments were electrophoretically separated in a 0.75% agarose gel and transferred to Zeta probe GT membrane by capillary action.[18]

Hybridization analysis with putative *S. neurona*-specific DNA probes was conducted at 65° C. for 12 h in 10 ml hybridization buffer (5×Denhardts, 4×SSC, 0.1% SDS at 65° C. for 30 min, and once in 0.5×SSC, 0.1% SDS for 30 min at the same temperature. The membranes were exposed to XAR-5 film at −70° C. for 24 h using lighting plus intensifying screens.

Random amplified polymorphic DNA assays using primer TGF generated a single DNA fragment with an electrophoretic mobility corresponding to 550 bp in all *S. neurona* isolates. The amplification of only a minute amount of product was detectable from isolate 3. A DNA fragment with an identical electrophoretic mobility was also amplified from the DNA of *S. campestris, E. falciformis, E. ahsata* and

*E. bovis*, but not from bovine monocyte cells. However, when the 550-bp DNA fragment from *S. neurona* (SN 2) was used as a probe, only those DNA fragments amplified from the *S. neurona* isolates hybridized.

Although 550-bp DNA fragments were also generated from other coccidia, the fragments did not share nucleotide sequence homology with *S. neurona*. Cross-species hybridization did not occur when the 550-bp DNA fragment from *S. neurona* (SN 2) was used to probe Southern transfers of genomic DNA isolated from bovine monocyte cells, *Escherichia coli. E. vermiformis, E. ahsata, E. nieschulzi, T. gondii, S. campestris* or *S. cruzi*.

The RAPD assay has been successfully used to differentiate among closely related organisms.[9,19–21] It was found that it is possible to identify unique RAPD fragments which could be used as species-specific DNA probes.

In the present study, the RAPD assay differentiated *S. neurona* from *S. cruzi* and *S. campestris*, as well as *T. gondii* and five Eimeria spp.

These data, among geographically distinct isolates of *S. neurona*, suggest that EPM is caused by a single organism. The 550-bp DNA fragment generated by the RAPD assay has been developed into a species-specific probe for *S. neurona*. The recognition of a putative DNA probe has facilitated the development of a diagnostic assay for *S. neurona* based on DNA hybridization.

Sarcocystis spp. have a heteroxenous, predator-prey or scavenger-carrion life cycle. The definitive host(s) and true intermediate host(s) of *S. neurona* are not known. Sarcocystis of *S. neurona*, required for transmission to the definitive host, have not been observed in the horse.[22] Consequently, the horse is considered an aberrant, dead-end host. *Sarcocystis neurona* probably cycles normally between two or more wildlife species. Although many species have been suggested as the true definitive host(s) of *S. neurona*, skunks, raccoons or opossums are the most probable. Similar to EPM, these species are broadly distributed but unique to the Western hemisphere. Small rodents or birds are speculative but reasonable candidates for the true intermediate host(s) of *S. neurona*.

While the RAPD assay and resultant probes have immediate application for the differentiation of *S. neurona* from other equine coccidia, an equally important use is the ability to discern and solve the parasite's life cycle by testing Sarcocystis spp. from potential hosts. The availability of infective stages will permit the experiments necessary to develop effective prevention and control measures for EPM.

REFERENCES

1. Fayer, R., Mayhew, I. G., Baird, J. D. et al. (1990). Epidemiology of equine protozoal myeloencephalitis in North America based on histologically confirmed cases. *Journal of Veterinary Internal Medicine* 4, 54–7.
2. MacKay, R. J. S., Davis, S. W. & Dubey, J. P. (1992). Equine protozoal myeloencephalitis. *The Compendium for Practicing Veterinarians* 14, 1359–66.
3. Granstrom, D. E., Dubey, J. P., Davis, S. W., Fayer, R., Fox, J. C., Poonacha, K. B., Giles, R. C. & Comer, P. F. (1993). Equine protozoal myeloencephalitis: antigen analysis of cultured *Sarcocystis neurona* merozoites. *Journal of Veterinary Diagnostic Investigation* 5, 88–90.
4. Granstrom, D. C. (1993). Diagnosis of equine protozoal myeloencephalitis: Western blot analysis. Proc. 11th ACVIM Forum, Washington D.C., May, 1993, Pp. 587–590.
5. Saiki, R. K., Gelfand, D. H., Stoffel, S., Scharf, S. J., Higuchi, R., Horn, G.t., Mullis, K. B. & Erlich, H. A. (1988). Primer directed enzymatic amplification of DNA with a thermostable DNA polymerase. *Science* 239, 487–91.
6. Williams, J. G. K., Kubelik, A. R., Livak, K. J., Rafalski, J. A. & Tingey, S. V. (1990). DNA polymorphisms amplified by arbitrary primers are useful as genetic markers. *Nucleic Acids Research* 18, 6531–5.
7. Welsh, J. & McClelland, M. (1990). Fingerprinting using PCR with arbitrary primers. *Nucleic Acids Research* 18. 7213–8.
8. MacPherson, J. M. & Gajadhar, A. A. (1993). Differentiation of seven Eimeria species by random amplified polymorphic DNA. *Veterinary Parasitology* 45, 257–66.
9. Procunier, J. D., Fernando, M. A. & Barta, J. R. (1993). Species and strain differentiation of Eimeria spp. of the domestic fowl using DNA polymorphisms amplified by arbitrary primers. *Parasitology Research* (in press).
10. Davis, S. W., Daft, B. M. & Dubey, J. P. (1991). Sarcocystis neurona cultured in vitro from a horse with equine protozoal myelitis. *Equine Veterinary Journal* 23, 315–7.
11. Davis, S. W., Speer, C. A. & Dubey, J. P. (1991). In vitro cultivation of *Sarcocystis neurona* from the spinal cord of a horse with equine protozoal myeloencephalitis. *Journal of Parasitology* 77, 789–92.
12. Granstrom, D. E., Alvarez, O., Dubey, J. P., Comer, P. F. & Williams, N. M. (1992). Equine protozoal myelitis in Panamanian horses and isolation of *Sarcocystis neurona*. *Journal of Parasitology* 78, 909–12.
13. Dubey, J. P. Davis, S. W., Speer, C. A., Bowman, D. D., de Lahunta, A., Granstrom, D. E., Topper, M. J., Hamir, A. N., Cummings, J. F. & Suter, M. M. (1991). *Sarcocystis neurona* n. sp. (Protozoa: Apicomplexa), the etiological agent of equine protozoal myeloencephalitis, *Journal of Parasitology* 77, 212–8.
14. Gajadhar, A. A., Marquardt, W. C., Hall, R., Gunderson, J. Ariztia-Carmona, E. V. & Sogin, M. L. (1991). Ribosomal sequences of *Sarcocystis muris, Theileria annulata* and *Crypthecodinium cohnii* reveal evolutionary relationships among apicomplexans, dinoflagellates, and ciliates. *Molecular and Biochemical Parasitology* 45, 147–54.
15. Yu, K & Pauls, K. P. (1992). Optimization of the PCR program for RAPD analysis. *Nucleic Acids Research* 20, 2606.
16. Sambrook, J., Fritsch, E. F. & Maniatis, T. (1989). *Molecular cloning. A Laboratory Manual*. New York: Cold Spring Harbor Laboratory Press.
17. Rigby, P. W., Dieckmann, M., Rhodes, C. & Berg, P. (1977). labelling deoxyribonucleic acid to high specific activity in vitro by nick translation with DNA polymerase 1. *Journal of Molecular biology* 113, 247–51.
18. Southern, E. M. (1975). Detection of specific sequences among DNA fragments separated by gel electrophoresis. *Journal of molecular Biology* 98, 503–17.
19. Crowhurst, R. N., Hawthorne, B. T., Rikkerink, E. H. A. & Templeton, M. D. (1991). Differentiation of *Fusarium solani* f. sp. cucurbitae races 1 and 2 by random amplification of polymorphic DNA. *Current Genetics* 20, 391–6.
20. Goodwin, P. H. & Annis, S. L. (1991). Rapid identification of genetic variation and pathotype of *Leptosphaeria maculans* by random amplified polymorphic DNA assay. *Applied and Environmental Microbiology* 57, 2482–6.
21. Jayarao, B. M., Bassam, B. J., Caetano-Anolls, G., Gresshoff, P. M. & Oliver, S. P. (1992). Subtyping of *Streptococcus uberis* by DNA amplification fingerprinting. *Journal of Clinical Microbiology* 30, 1347–50.

22. Dubey, J. P., Speer, C. A. & Fayer, R. (1989). *Sarcocystosis of Animals and Man*. Boca Raton: CRC Press.

Barta, J. R. 1989. Phylogenetic analysis of the class Sporozoea (Phylum Apicomplexa Levine, 1970): evidence for the independent evolution of heteroxenous life cycles. J Parasitol. 75: 195–206.

Barta, J. R., Jenkins, M. C., and Danforth, H. D. 1991. Evolutionary relationships of avian Elmena species among other Apicomplexan protozoa: Monophyly of the Apicomplexa is supported. Mol. Biol. Evol. 8: 345–355.

Beech, J. and Dodd. D. C. 1974. Toxoplasma-like encephalomyelitis in the horse. Vet. Pathol. 11: 87–96.

Cusick, P. K., Sells, D. M., Hamilton, D. P. and Hardenbrook, H. J. 1974. Toxoplasmosis in two horses. J. Am. Vet. Med. Assoc. 164: 77–80.

Davis, S. W., Speer, C. A. and Dubey, J. P. 1991. In vitro cultivation of *Sarcocystis neurona* from the spinal cord of a horse with equine protozoal myelitis. J. Parasitol. 77: 789–792.

Dubey, J. P. 1974. Toxoplasmosis in horses. J. Am. Vet. Med. Assoc. 165: 801–802.

Dubey, J. P. Davis, G. W., Koestner, A. and Kiryu, K. 1974. Equine encephalomyelitis due to a protozoan parasite resembling *Toxoplasmna gondii*. J. Am. Vet. Med. Assoc. 165: 249–255.

Dubey, J. P., Davis, S. W., Speer, C. A., Bowman, D. D., de Lahunta, A., Granstrbm, D. E., Topper, M. J., Hamir, A. N., Cummings, J. F. and Suter, M. M. 1991. *Sarcocystis neurona* n. sp. (protozoa: apicomplexa), the etiological agent of equine protozoal myeloencephalitis. J. Parasitol. 77: 212–218.

Elwood, H. J., Olsen G. J., and Sogin, M. L. 1985. The small subunit ribosomal RNA gene sequences from the hypotrichous ciliates *Oxytricha nova* and *Stylonchia pustulata*. J. Mol. Biol. and Evol. 2: 399–410.

Felsenstein, J. 1982. Numerical methods for inferring evolutionary trees. Q. Rev. Biol. 57: 379–404.

Felsenstein, J. 1989. PHYLIP Phylogeny inference package (Version 3.2). Cladistics 5, 164–166.

Gajadhar, A. A., Marquardt, W. C., Hall, R., Gunderson, J., Ariztia-Carmona, E. V., and Sogin, M. L. 1990. Ribosomal RNA sequences of *Sarcocystis muris, Theileria annulata* and *Crypthecodinum cohnii* reveal evolutionary relationships among apicomplexans, dinoflagellates, and ciliates. Mol. Biochem. Parasitol. 45:147–154.

Johnson, A. M., Illana, S. Hakendorf, P., and Baverstock, P. R. 1988. Phylogenetic relationships of the Apicomplexan protist Sarcocysdts as determined by small subunit ribosoma RNA comparison. J . Parasit. 74: 847–860.

Krowczynska A. M. and Henderson M. B. 1992. Efficient purification of PCR products using ultrfitration. BioTechniques 13: 286–289.

Levine, N. D., Corliss, J. O., Cox, F. E. G., Deroux, G., Grain, J., Honigberg, B. M. Leedale, G. F., Loeblich, A. R., Lom, J., Lynn, D., Merinfeld, E. G., Page, F. C., Poljansky, G., Sprague, V., Vayra, J., and Wallace, F. G. 1980. A newly revised classification of the protozoa. J Protozool. 27: 27–58.

Medlin, L., Elwood H. J., Stickel S. and Sogin, M. L. 1988. Sequence analysis of enzymatically amplified genomic small subunit rRNA genes from the diatom, *Skeletonema pustulata*. Gene 71: 491–499.

Tenter A. M., Vietmeyer C., Thummel P., and Rommel M. 1991. Antigenic characterisation of monoclonal antibodies against *Sarcocystis muris* by western blotting and immuno-electronmicroscopy. Parasitol Res 77(3): 217–23.

Mullis, K. 1991. The polymerase chain reaction in an anemic mode: how to avoid cold oligodeoxyribonuclear fusion. PCR Methods Appl. 1: 1–4.

Neefs, J., Van de Peer, Y., Hendriks, L. and De Wachter, R. 1990. Compilation of small ribosomal subunit RNA sequences. Nuc Acids Res 18, Suppl.: 2237–2317.

Saiki, R. K., Gelfand, D. H., Stoffel, S., Scharf, S. J., Higuchi, R., Horn, G. T., Mullis, K. D. and Elrich, H. A. 1988. Primer-directed enzymatic amplification of DNA with a thermostable DNA polymerase. Science 239: 487–491.

Sambrook, J., Fritsch, E. F. and Maniatis, T. 1989. Molecular Cloning, a Laboratory Manual. 2nd Ed. Cold Spring Harbor Laboratory Press, New York.

Schuler, G. D., Altschul, S. F. and Lipman, D. J. 1991. A workbench for multiple alignment construction and analysis. Proteins Struct. Funct. Genet. 9: 180–190.

Simpson, C. P. and Mayhew, I. G. 1980. Evidence for Sarcocystis as the etiologic agent of equine protozoal encephalomyelitis. J. Protozool. 27: 288–292.

Sogin, M. L. 1989. Evolution of eukaryotic microorganisms and their small subunit ribosomal RNAs. Am. Zool. 29:487–499.

Tenter, A. M., Baverstock, P. R. and Johnson, A. M. 1992. Phylogenetic relationships of Sarcocystis species from sheep, goats, cattle and mice based on ribosomal RNA sequences. Int. J. Parasitol. 22: 503–513.

Zuckerkandl, E. and Pauling L. 1965. Molecules as documents of evolutionary history. J. Theor. Biol. 8: 357–366.

In sum, the present invention provides a specific amplification primer/probe which can be used in an in vitro diagnostic test for the presence of *S. neurona* in equine blood or cerebrospinal fluid. *Sarcocystis neurona* is responsible for the equine condition of protozoal myelitis.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A diagnostic primer consisting of nucleotide positions 1470–1487 of the small ribosomal subunit of *Sarcocystis neurona.*

2. The primer according to claim 1, wherein said primer has a sequence as shown in SEQ ID NO:1, 5'-CCATTCCGGACGCGGGT-3'.

3. The primer according to claim 1, wherein said primer is coupled to a detectable label.

4. The primer according to claim 3, wherein said detectable label is selected from the group consisting of chromophores, fluorophores, chemiluminescent materials and radioisotopes.

5. The primer according to claim 4, wherein said detectable label is a radioisotope.

6. A method for the diagnosis of Equine protozoal myeloencephalitis (EPM) comprising the steps of (a) contacting a equine cerebrospinal fluid specimen with a primer according to claim 3;

(b) removing unreacted sample from the specimen; and (c) detecting the detectable label hybridized to the specimen, where the presence of a detectable label hybridized to the specimen is indicative of EPM.

7. A method for the diagnosis of Equine protozoal myeloencephalitis (EPM) comprising the steps of obtaining equine cerebrospinal fluid and testing for the presence of *Sarcocystis neurona* with the primer of SEQ ID NO:1, where the presence of *Sarcocystis neurona* is indicative of EPM.

8. A method for the diagnosis of Equine protozoal myeloencephalitis according to claim 7, wherein said step of testing for the presence of *Sarcocystis neurona* is testing by nested polymerase chain reaction.

9. A method for the diagnosis of Equine protozoal myeloencephalitis according to claim 8, wherein said nested polymerase chain reaction comprises two stages and employs the primer pairs a–d, a) primer 1470R, reverse primer, first stage, 5' CCATTCCGGACGCGGGT-3'(SEQ ID NO:1);

b) primer 1184F, forward primer, first stage, 5' CCAGGCGTGGAGCTGCG-3'(SEQ ID NO:4);

c) primer 1055F, forward primer, second stage, 5' GGTGGTGGTGCATGGCCG-3'(SEQ ID NO:5); and d) primer 1475R, reverse primer, second stage, 5' GCGCGTGGCCCAGAAC-3'(SEQ ID NO:6).

10. A method for the diagnosis of Equine protozoal myeloencephalitis (EPM) comprising the steps of obtaining equine cerebrospinal fluid and testing for the presence of *Sarcocystis neurona* with a ribosomal RNA primer or probe from *Sarcocystis neurona* a consisting of nucleotide positions 1470–1487 or derivatives thereof in which 1–5 nucleotides are added to the 3' end of the primer or probe, where the presence of *Sarcocystis neurona* is indicative of EPM.

* * * * *

SEQUENCE LISTING (1) GENERAL INFORMATION:

(iii) NUMBER OF SEQUENCES: 97

(2) INFORMATION FOR SEQ ID NO:1:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CCATTCCGGA CGCGGGT                                                        17

(2) INFORMATION FOR SEQ ID NO:2:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GGATTTCGGT TCTATTTTGT TGG                                                 23

(2) INFORMATION FOR SEQ ID NO:3:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GTTTCAGCCT TGCGACCAT                                                      19

(2) INFORMATION FOR SEQ ID NO:4:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CCAGGCGTGG AGCTGCG                                                        17

(2) INFORMATION FOR SEQ ID NO:5:

(i) SEQUENCE CHARACTERISTICS:
         (A) LENGTH: 18 base pairs (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GGTGGTGGTG CATGGCCG                           18

(2) INFORMATION FOR SEQ ID NO:6:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

GCGCGTGGCC CAGAAC                             16

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

GCACGAACGC GCCACAAA                           18

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

ATAGTAACCG AACGGATCGC ATTAT                   25

(2) INFORMATION FOR SEQ ID NO:9:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

ATAGTAACCG AACGGATCGC ACTAT                                                  25

(2) INFORMATION FOR SEQ ID NO:10:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

ATNTCGCNNT CTGAGATCGC GATNAT                                                 26

(2) INFORMATION FOR SEQ ID NO:11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

NTANNANTCC GNNNGGTTCN NNTNANT                                                27

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

ATAGTAACCG AACGGATCGC ATTAT                                                  25

(2) INFORMATION FOR SEQ ID NO:13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

ATAGTANCNG AACGGATCGC ATCATAT                                            27

(2) INFORMATION FOR SEQ ID NO:14:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

ATNGTNNTCC GTTCNTTCGT CATTNT                                             26

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

ATAGTAACCG AACGGGTCGC GTTGACT                                            27

(2) INFORMATION FOR SEQ ID NO:16:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

ATAGTAACCG AACGGATCGC ANGTT                                              25

(2) INFORMATION FOR SEQ ID NO:17:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

ATAATAACTT TNCGGATCAC ATTAAAT                                                        27

(2) INFORMATION FOR SEQ ID NO:18:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

GCGATGGATC ATTCAAGTTT CTGACCTATC AGCTTTCGAC GGTACTGTA                                 49

(2) INFORMATION FOR SEQ ID NO:19:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

GCGATAGATC ATTCAAGTTT CTGACCTATC AGCTTTCGAC GGTACTGTA                                 49

(2) INFORMATION FOR SEQ ID NO:20:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GCGATNNNNN NTNCNNGTTT CTGNCCTATC NNGCTTTCNG NCGGTAGTGT A                              51

(2) INFORMATION FOR SEQ ID NO:21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

-continued

```
GCGTTNGATC ATTCNNGTTT CTGACCTATC NAGCTTTNGA NCGGTNGTGT N        51

(2) INFORMATION FOR SEQ ID NO:22:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

GCGATAGATC NTTCAAGTTT CTGACCTATC AGCTTTCGAC GGTNGTGTA            49

(2) INFORMATION FOR SEQ ID NO:23:

(i) SEQUENCE CHARACTERISTICS:
         (A) LENGTH: 49 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

GCGATAGATC ATTCAAGTTT CTGACCTATC AGCTTTCNAC GGTACTGTA            49

(2) INFORMATION FOR SEQ ID NO:24:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

GCGNNGGATN NNNTCGANTN TCTNGACTCT ATCNGCTTCG CGGTAGTGTA           50

(2) INFORMATION FOR SEQ ID NO:25:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

GCGACGGATC ATTCAAGTTT CTGACCTATC AGCTATTCGA CGGNACTGTA           50
```

(2) INFORMATION FOR SEQ ID NO:26:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GCGATGGATC ATTNAAGNTT CTGACCTATC NAGCTTTCGA CGGTAGGNTA          50

(2) INFORMATION FOR SEQ ID NO:27:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GTGACATATC ATTCAAGTTT CTGACCTATC AGCTTTAGNC GGTAGGNTA           49

(2) INFORMATION FOR SEQ ID NO:28:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

TTGGACTACC GTGGCAGTGA CGGGTAACGG GGAATTAGGG TTCGATTCCG G        51

(2) INFORMATION FOR SEQ ID NO:29:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

TTGGACTACC GTGGCAGTGA CGGGTAACGG GGAATTAGGG TTCGATTCCG G        51

(2) INFORMATION FOR SEQ ID NO:30:

(i) SEQUENCE CHARACTERISTICS:

(A) LENGTH: 50 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

TTGGCTCCCG TGGCNGTGNN NGGTNNNGGG GNATTAGGGT TCGNTTCCGG          50

(2) INFORMATION FOR SEQ ID NO:31:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

TTNGGACTAC CGTGGCAGTG NCGGGNNNCG GGGNATTAGG GTTCGATTCC GG        52

(2) INFORMATION FOR SEQ ID NO:32:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

TTGGNCTNCN TNGCAGTGNC GGNNNCGGGG NNTTAGGGNT CGNNTCCGG           49

(2) INFORMATION FOR SEQ ID NO:33:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

TTGGACTACC NTGGCAGNGA CGGGNNACGG GGAATTAGGG TTCGATTCCG G         51

(2) INFORMATION FOR SEQ ID NO:34:

(i) SEQUENCE CHARACTERISTICS:
        (A) LENGTH: 49 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

TTGGCTNCNN TNGCAGTGNG GNTNNNGGGG AATTCGGGTT CGATTCCGG                49

(2) INFORMATION FOR SEQ ID NO:35:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

TTGGACTACC NTGGCAGNGA CGGNTAACGG GGAATNAGNN NTNNATTCCG N              51

(2) INFORMATION FOR SEQ ID NO:36:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

NTGGCCTACN NTNGCAGTGA CGGGNNACGG GGAATTAGGG TTCGATTCCG G              51

(2) INFORMATION FOR SEQ ID NO:37:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

TTGGCCTCAC NNGGCAATGA CGGGTACNNG GGAATTAGGN NTCGATTCCA GG             52

(2) INFORMATION FOR SEQ ID NO:38:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

AGAGGGAGCC TGAGAAACGG CTACCACATC TAAGGAAGGC AGCAGGCGCG CA          52

(2) INFORMATION FOR SEQ ID NO:39:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

AGAGGGAGCC TGAGAAACGG CTACCACATC TAAGGAAGGC AGCAGGCGCG CA          52

(2) INFORMATION FOR SEQ ID NO:40:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

AGAGGGAGCC TGAGANNCGG CTNCCNCNTC TNNGGNNGGC NGCNGGCGCG CA          52

(2) INFORMATION FOR SEQ ID NO:41:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

AGNTGGGAGC CTGAAANNCG GCTNCCACAT CTNNNNGGCN GCNGGCGCNC A          51

(2) INFORMATION FOR SEQ ID NO:42:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

AGNGGGAGCC TGAGNNNCGG CTNCCNCNTC TNNNGNNGGC NNNNNNNNNN CA            52

(2) INFORMATION FOR SEQ ID NO:43:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

AGAGGGAGCC TGAGAANCGG CTACCACATC TAAGGNGGCA GCAGGCGCNC A             51

(2) INFORMATION FOR SEQ ID NO:44:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

AGAGGGAGCC TGAGNNNCGG CTACCACATC TNNNNNGGCN GCNGGCGCNC A             51

(2) INFORMATION FOR SEQ ID NO:45:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

AGANNGAGNC TGANAAACGG CTACCACATC TAAGGAAGGC AGCAGGCGCG CA            52

(2) INFORMATION FOR SEQ ID NO:46:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

```
AGAGGGAGCC TGAGAAACGG CTACCNNATC TAAGGNNGGC AGCAGGCGCG CA            52

(2) INFORMATION FOR SEQ ID NO:47:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

ANAGGGAGCC TCGAGAAACG GCTACCACAT NTAAGGAAGG CAGCAGGCGC NCA           53

(2) INFORMATION FOR SEQ ID NO:48:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:48:

ACACTGGAAA TTATATTTCT AGTGATTGGA ATGATGGGAA TCCAAACCCC TTT           53

(2) INFORMATION FOR SEQ ID NO:49:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:49:

ACACTGGAAA TTCAATTTCT AGTGATTGGA ATGATGGGAA TCCAAACCCC TTT           53

(2) INFORMATION FOR SEQ ID NO:50:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:50:

ACACTGGAAA TTCAATTTCT AGTNATTGGA ATGATGGGNA TTTNNNCCCC TTT           53
```

(2) INFORMATION FOR SEQ ID NO:51:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:51:

ACNCTGGAAA TTTTNTTTCT NGTGATTGGA ATGATGGGAA TTTNNNCCCC TTT      53

(2) INFORMATION FOR SEQ ID NO:52:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:52:

ACACTGGAAA TTTTNTTTCT AGTNATTGGN ATGANGGGNA TTTNNNCCCN TTT      53

(2) INFORMATION FOR SEQ ID NO:53:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:53:

ACNCNTGGAA ATTGTNTTTC TAGTGATTGG AATGATGGGA ATCCNNNCCC CTTT      54

(2) INFORMATION FOR SEQ ID NO:54:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:54:

ACACTGGAAA TTTTATTTCT AGTNATTGGA ATGATGGGAA TTTNNNCCCN TTT      53

(2) INFORMATION FOR SEQ ID NO:55:

(i) SEQUENCE CHARACTERISTICS:
    (A) LENGTH: 53 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:55:

ACACTGGAAA TTTCATTTCT AGTGATTGGA ATGATAGGAA TCCAAACCCC TTT    53

(2) INFORMATION FOR SEQ ID NO:56:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:56:

ATACAGGGNA TTTTATGCTT TGTAATTGGA ATGATGGGAA TGTAAAACCC TTN    53

(2) INFORMATION FOR SEQ ID NO:57:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:57:

ATANCTAGGN CTTTTTGGTT TTGTNATTGT GAATGATGTT AATGTATNCC CCTTT    55

(2) INFORMATION FOR SEQ ID NO:58:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:58:

ATTTAACTGT CAGAGGTGAA ATTCTTAGAT TTGTTAAAGA CGAACTACTG C    51

(2) INFORMATION FOR SEQ ID NO:59:

(i) SEQUENCE CHARACTERISTICS:
        (A) LENGTH: 51 base pairs
        (B) TYPE: nucleic acid (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:59:

ATTTAACTGT CAGAGGTGAA ATTCTTAGAT TTGTTAAAGA CGAACTACTG C        51

(2) INFORMATION FOR SEQ ID NO:60:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:60:

ATTTAACTNN AGAGGTGAAA ATCTTAGATT TGTTAAAGAC GACCTNCTGC           50

(2) INFORMATION FOR SEQ ID NO:61:

(i) SEQUENCE CHARACTERISTICS:
         (A) LENGTH: 52 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:61:

ATTTAACTNT NAGAGGTGAA ATTCTTAGAT TTGTTAAAGA CGNANCTNCT GC        52

(2) INFORMATION FOR SEQ ID NO:62:

(i) SEQUENCE CHARACTERISTICS:
         (A) LENGTH: 50 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:62:

ATTTAACTNN AGAGGTGAAA TTCTTAGATT TGTTAAAGNC GANCTNCTGC           50

(2) INFORMATION FOR SEQ ID NO:63:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:63:

ATTTAACTGN NAGAGGTGAA ATTCTTAGAT TTGTTAAAGA CGAACTACTG C         51

(2) INFORMATION FOR SEQ ID NO:64:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:64:

ATTTANCTNN NAGAGGTGAA ATTCTTAGAT TTGTTAAAGA CGACCTACTG C         51

(2) INFORMATION FOR SEQ ID NO:65:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:65:

ATTTAACTGT CAGAGGTGAA ATTCTTAGAT TTGTTAAAGA CGACTACTGC           50

(2) INFORMATION FOR SEQ ID NO:66:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:66:

ATTTAACTGN NAGAGGTGAA ATTCTTAGAT TTGTTAAAGA CGAACCTACT GC        52

(2) INFORMATION FOR SEQ ID NO:67:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO

6,110,665

49

-continued (iv) ANTI-SENSE: NO (xi) SEQUENCE DESCRIPTION: SEQ ID NO:67:

ATTTAACAGT CAGAGGTGAA ATTCTTGAGT TTGTTAAAGA CAAACTAATG C      51

(2) INFORMATION FOR SEQ ID NO:68:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:68:

GAAAGCATTT GCCAAAGATG TTTTCATTAA TCAAGAACGA AAGTTAGGGG CTC      53

(2) INFORMATION FOR SEQ ID NO:69:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:69:

GAAAGCATTT GCCAAAGATG TTTTCATTAA TCAAGAACGA AAGTTAGGGG CTC      53

(2) INFORMATION FOR SEQ ID NO:70:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:70:

GAAAGCATTT GCCAAAGATG TTTTCATTAA TCAAGAACGA AAGNNNGGGN CTC      53

(2) INFORMATION FOR SEQ ID NO:71:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:71:

GAAAGCATTT GCCAAAGATG TTTTCATTNA TCAAGAACGA AAGTNNGGGN CTC          53

(2) INFORMATION FOR SEQ ID NO:72:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:72:

GAAAGCATTT GCCAAAGATG TTTTCATTAA TCAAGAACGA AAGTTAGGGN CTN          53

(2) INFORMATION FOR SEQ ID NO:73:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:73:

GAAAGCATTT GCCAAAGATG TTTTCATTAA TCAAGAACGA AAGTTAGGGG CTC          53

(2) INFORMATION FOR SEQ ID NO:74:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:74:

GAAAGCATTT GCCAAAGATG TTTTCATTAA TCAAGAACGA AAGTTNGGGN CTN          53

(2) INFORMATION FOR SEQ ID NO:75:

(i) SEQUENCE CHARACTERISTICS:
            (A) LENGTH: 53 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:75:

GAAAGCATTT GCCAAAGATG TTTTCATTAA TCAAGAACGA AAGTTAGGGG CTC          53

(2) INFORMATION FOR SEQ ID NO:76:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:76:

GAAAGCATTT GCCAAGGATG TTTTCATTAA TCAAGACCGA CAGTAGGGGG TTT      53

(2) INFORMATION FOR SEQ ID NO:77:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:77:

GAAAGCATTT GCCAAGGATN TTTTCATTAA TCAAGANNGA AAGTTAGGGG ATC      53

(2) INFORMATION FOR SEQ ID NO:78:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:78:

GAAGACGATC AGATACCGTC GTAGTCTTAA CCATAAACTA TGCCGACTAG AG      52

(2) INFORMATION FOR SEQ ID NO:79:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:79:

GAAGACGATC AGATACCGTC GTAGTCTTAA CCATAAACTA TGCCGACTAG AG      52

(2) INFORMATION FOR SEQ ID NO:80:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:80:

GAAGNCGATC AGATACCGTC GTAGTCTTAA CCATAAACTA TGCCGACTAG AG          52

(2) INFORMATION FOR SEQ ID NO:81:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:81:

GAAGCGATCA GATACCGTCG TAGTCTTAAC CATAAACTAT GCCGACTAGA G           51

(2) INFORMATION FOR SEQ ID NO:82:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:82:

GNAGNCGATC NGNTNNCGTC GTAGTCNTAN CCATNNACTA TGNCGACTAG AG          52

(2) INFORMATION FOR SEQ ID NO:83:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:83:

GAAGACGATC AGATACCGTC GTAGTCTTAA CCATAAACTA TGCCGACTAG AG          52

(2) INFORMATION FOR SEQ ID NO:84:

(i) SEQUENCE CHARACTERISTICS:
            (A) LENGTH: 52 base pairs

```
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:84:

GNAGNCGATN NGATNCGTNG TNGTCTTNNN CATNNNCTAT GNCGANCTNG AG         52

(2) INFORMATION FOR SEQ ID NO:85:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:85:

GAAGACGATC GATACCGTCG TAGTCTTAAC CATAAACTAT GCCGACTAGA G          51

(2) INFORMATION FOR SEQ ID NO:86:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:86:

GAAGACGATT AGATACCGTC GTAATCTCTA CCATAAACTA TGCCGACTAG AG         52

(2) INFORMATION FOR SEQ ID NO:87:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:87:

GAAGACGATC AGATACCGTC GTAGTCTTAA CCATAAACTA TGCCAACTAG AG         52

(2) INFORMATION FOR SEQ ID NO:88:

(i) SEQUENCE CHARACTERISTICS:
            (A) LENGTH: 45 base pairs
            (B) TYPE: nucleic acid
            (C) STRANDEDNESS: single
            (D) TOPOLOGY: linear
```

(ii) MOLECULE TYPE: DNA (genomic)

(iii) HYPOTHETICAL: NO (iv) ANTI-SENSE: NO (xi) SEQUENCE DESCRIPTION: SEQ ID NO:88:

ATAGGAAAAC GTCATCCTTG ACTTCTCCTG CACCTTATGA GAAAT         45

(2) INFORMATION FOR SEQ ID NO:89:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:89:

ATAGGAAAAA GTCATCCTTG ACTTCTCCTG CACCTTATGA GAAAT         45

(2) INFORMATION FOR SEQ ID NO:90:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:90:

ATAGGAAAAT GTCATTTTGC TGNCNTCTCC TNCACCTTAT GAGNNAT         47

(2) INFORMATION FOR SEQ ID NO:91:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:91:

ATAGGAAAAT GTCATTTTGC TGNCTTCTCC TNCNCCTTAT GAGAAAT         47

(2) INFORMATION FOR SEQ ID NO:92:

(i) SEQUENCE CHARACTERISTICS:
            (A) LENGTH: 47 base pairs
            (B) TYPE: nucleic acid
            (C) STRANDEDNESS: single
            (D) TOPOLOGY: linear (ii) MOLECULE TYPE: DNA (genomic)

-continued (iii) HYPOTHETICAL: NO (iv) ANTI-SENSE: NO (xi) SEQUENCE DESCRIPTION: SEQ ID NO:92:

ATAGGNAAAT NTCATTTTCT GNCTTCTCCT NCACCTTATG AGAAAGT                47

(2) INFORMATION FOR SEQ ID NO:93:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:93:

ATAGGAAATG TCACATTGTT GCTTCTCCCA CCTTATGAGA AAT                43

(2) INFORMATION FOR SEQ ID NO:94:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:94:

ATNGGANNAT GTNATTTTNC TNCNTCTCCN NCNCCTTATG AGAAAT             46

(2) INFORMATION FOR SEQ ID NO:95:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:95:

ATAGGAAAAC GTCATGCTTG ACTTCTCCTG CACCTTATGA GAAAT              45

(2) INFORMATION FOR SEQ ID NO:96:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO

-continued

```
    (xi) SEQUENCE DESCRIPTION: SEQ ID NO:96:

ATAGGGAAAC GCCTACCTTG GNNTCTCCTG CACCTCATGA GAAAT                    45

(2) INFORMATION FOR SEQ ID NO:97:

(i) SEQUENCE CHARACTERISTICS:
          (A) LENGTH: 44 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:97:

ATTGGNGNTT GTTTTCCTTA CTCCTTCAGC ACCTTATGAG AAAT                     44
```